United States Patent [19]

Hung et al.

[11] Patent Number: 5,110,938

[45] Date of Patent: May 5, 1992

[54] HALODIOXOLANE-CONTAINING OXAZINES AND OXAZOLINES, AND THEIR POLYMERS

[75] Inventors: Ming-Hong Hung; Mureo Kaku, both of Wilmington, Del.

[73] Assignee: E. I. Du Pont de Nemours and Company, Wilmington, Del.

[21] Appl. No.: 621,680

[22] Filed: Nov. 30, 1990

[51] Int. Cl.$^5$ ............................ C07D 263/14
[52] U.S. Cl. ..................... 548/237; 544/96; 549/430; 528/402
[58] Field of Search ................ 548/237; 544/96; 549/430

[56] References Cited

U.S. PATENT DOCUMENTS

| | | | |
|---|---|---|---|
| 2,490,392 | 12/1949 | Whutstone | 544/96 |
| 2,714,082 | 7/1955 | Davies et al. | 548/237 |
| 3,198,754 | 8/1965 | Ahlbrecht et al. | |
| 3,293,245 | 12/1966 | Litt et al. | |
| 3,300,274 | 1/1967 | Pittman et al. | |
| 3,373,194 | 3/1968 | Fuhrmann et al. | |
| 3,442,904 | 5/1969 | Middleton et al. | 548/237 |
| 3,458,456 | 7/1969 | Levy et al. | |
| 3,483,141 | 12/1969 | Litt et al. | |
| 3,523,123 | 8/1970 | Wehrmeister | 548/237 |
| 3,542,699 | 11/1970 | Levy et al. | 548/237 |
| 3,575,890 | 4/1971 | Litt et al. | |
| 3,681,329 | 8/1972 | Litt et al. | |
| 3,953,432 | 4/1976 | Wehrmeister | 548/237 |
| 4,079,062 | 3/1978 | Van Reet et al. | 549/430 |
| 4,176,073 | 11/1979 | Ryer et al. | 548/237 |
| 4,981,974 | 1/1991 | Dandreaux et al. | 548/238 |

OTHER PUBLICATIONS

Tanaka et al., Inorg. Chem., vol. 19, pp. 2612-2614 (1980).

*Primary Examiner*—Donald G. Daus

[57] ABSTRACT

Chloro- and fluorosubstituted dioxolane containing oxazolines and oxazines, and their polymers are disclosed. The polymers are useful for surface modification of other polymers.

13 Claims, No Drawings

HALODIOXOLANE-CONTAINING OXAZINES AND OXAZOLINES, AND THEIR POLYMERS

FIELD OF INVENTION

Chloro- and fluorosubstituted dioxolane containing oxazolines and oxazines, and their polymers are disclosed. The polymers are useful for surface modification of other polymers.

BACKGROUND OF THE INVENTION

Oxazolines and oxazines that are substituted with halogenated groups and their polymers are known, see for example U.S. Pat. Nos. 3,293,245, 3,458,456, 3,483,141, 3,575,890, and 3,681,329. None of these patents mentions substituted oxazolines or oxazines or their polymers in which the halogenated group is an aliphatic cyclic structure.

Polymers made from the ring opening polymerization of N-acyl aziridines have the same structure as those made from 2-substituted oxazolines. Poly(N-acyl aziridines) which contain pendant halogenated groups are known, see for example U.S. Pat. Nos. 3,198,754, 3,300,274 and 3,373,194. None of these patents mentions polymers in which the halogenated group is an aliphatic cyclic structure.

Many of the polymers, particularly the fluorinated polymers, disclosed in the aforementioned patents are only difficulty soluble, particularly in the more common organic solvents. It is an object of this application to provide polymers (and the monomers from which the polymers are made) which can modify the surface properties of other polymers, and which are readily soluble in common organic solvents. This solubility allows the instant polymers to be readily coated onto the surfaces of other polymers.

SUMMARY OF THE INVENTION

This invention concerns a compound of the formula

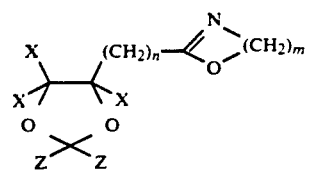

wherein:
each X is independently hydrogen, chlorine or fluorine;
each Z is independently —$CY_3$, —$C_2Y_5$, normal —$C_3Y_7$, fluorine, or chlorine;
m is 2 or 3;
n is zero or an integer of 1 to 10;
each Y is independently chlorine or fluorine; and provided that at least one of Y is fluorine.

This invention also concerns a polymer comprising the repeating unit

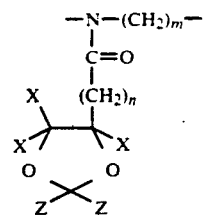

wherein:
each X is independently hydrogen, chlorine or fluorine;
each Z is independently —$CY_3$, —$C_2Y_5$, normal —$C_3Y_7$, fluorine, or chlorine;
m is 2 or 3;
n is zero or an integer of 1 to 10;
each Y is independently chlorine or fluorine; and provided that at least one of Y is fluorine.

DETAILS OF THE INVENTION

The compounds of this invention may be synthesized by a variety of methods. For the purposes of synthesis, the molecules may be considered as having three parts, an oxazoline or oxazine ring, a halosubstituted dioxolane ring, and a divalent alkylene group or a covalent bond connecting the two rings.

The formation of the oxazoline and oxazine rings (in the formulas for the compound above, where m is 2, it is an oxazoline, and where m is 3, it is an oxazine) is illustrated by the Examples herein, and/or in U.S. Pat. Nos. 3,293,245, 3,458,456, 3,483,141, 3,575,890, and 3,681,329, which are hereby included by reference. The synthesis of the dioxolane ring part of the molecule, containing a group that can be used in the formation of the connecting group, is illustrated herein and in U.S. Pat. Nos. 4,908,461 and 4,399,264 and commonly assigned U.S. patent applications 07/401,668, filed Aug. 30, 1989, and 450,351, filed Dec. 11, 1989, all of which are hereby included by reference. Other methods for the synthesis of these rings will be apparent to those skilled in the art.

The synthesis of the connecting group is illustrated in the Examples herein. These Examples show the synthesis of connecting groups where the number of methylene groups ("n") is 0 or 2. The following equations are illustrative of the synthesis of connecting groups containing differing numbers of methylene groups. Combinations and/or iterations of the various methods will yield various sized connecting groups. Other methods will be apparent to those skilled in the art.

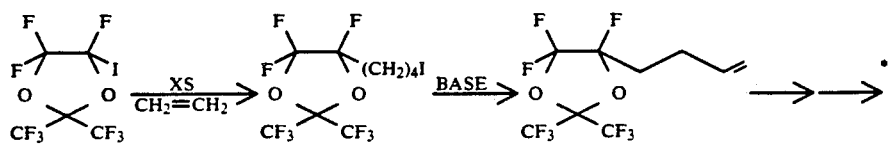

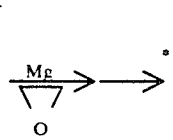
-continued

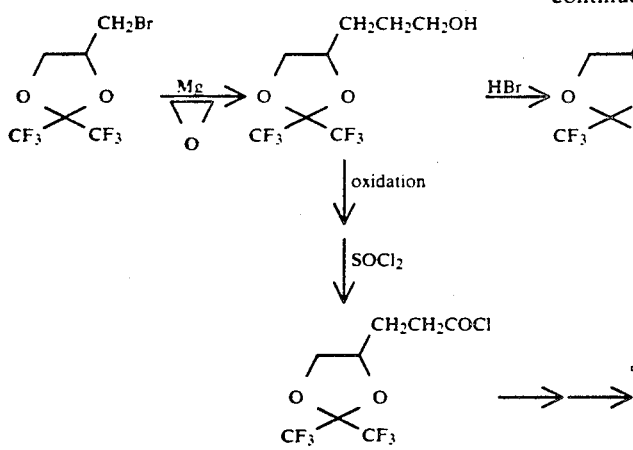

*Indicates procedures similar to those here or in Examples leading to oxazolines In a preferred compound m is 2. In another preferred compound each X is independently fluorine or hydrogen. In another preferred compound both groups Z are —CY₃. In another preferred compound Y is fluorine. In yet another preferred compound n is 0, 2, or 4. In an especially preferred compound all groups X are either fluorine or hydrogen. In another especially preferred compound both groups Z are —CF₃. Combinations of these preferred or especially preferred structural elements in the compounds are also preferred. Particularly preferred compounds are 2-{2-[perfluoro(2,2-dimethyl-4-dioxolanyl)]ethyl}oxazoline and 2-[2,2-bis(trifluoromethyl)-4-dioxolanyl]oxazoline.

The compounds of the present invention are useful as monomers to prepare the polymers described below.

The polymers of this invention may be prepared by the polymerization of the above described monomers, or the corresponding N-acyl aziridines. Polymers may be prepared from the oxazolines and oxazines by cationic polymerization. Polymerization methods for oxazolines and oxazines are described in the Examples and/or in U.S. Pat. Nos. 3,458,456, 3,483,141, and 3,575,890. Polymerization methods for N-acyl aziridines are described in U.S. Pat. Nos. 3,198,754, 3,300,274 and 3,373,194, which are hereby included by reference.

By the term "comprising the repeating unit", above, is meant that the polymers of this invention may be homopolymers [contain only one type (formula) of monomer unit], or a copolymer containing more than one type of the monomer units shown above and/or contain other monomer units, such as other oxazolines or oxazines, for example 2-methyloxazoline or 2-phenyloxazine.

In a preferred polymer, m is 2. In another preferred polymer each X is independently fluorine or hydrogen. In another preferred polymer both groups Z are —CY₃. In another preferred polymer Y is fluorine. In yet another preferred polymer n is 0, 2, or 4. In an especially preferred polymer all groups X are either fluorine or hydrogen. In another especially preferred polymer both groups Z are —CF₃. Combinations of these preferred or especially preferred structural elements in the polymers are also preferred. Particularly preferred polymers contain the repeat unit.

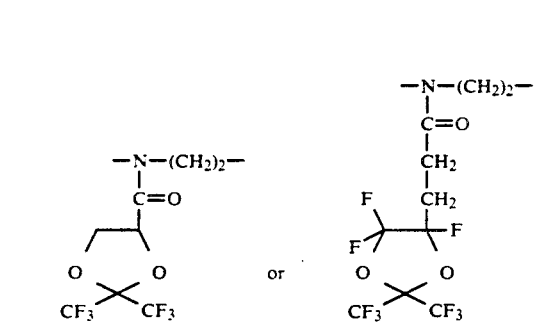

The polymers are useful to modify the surface properties of other polymers, or may act as compatabilizers between two other polymers. In particular the polymers which contain highly fluorinated dioxolane moieties render other polymer surfaces hydrophobic. The polymers of the present invention may be used to modify the surface properties of other polymers by melt mixing the two polymers, or preferably by solution coating the polymer of this invention onto the surface of the polymer whose properties are to be modified. The polymers of the instant invention are more soluble in common organic solvents than many of the prior art fluorinated polymers made from N-acyl aziridines, oxazolines and oxazines. Such prior art polymers have been described as being useful for surface modification (U.S. Pat. Nos. 3,300,274 and 3,575,890 for example). The instant polymers are useful for modifying the surface properties of films or natural or synthetic fibers, by solution coating such films or fibers. Natural or synthetic fibers coated with the instant polymers may exhibit better stain and/or water resistance.

In the following Examples, these abbreviations are used:
 GPC—gel permeation chromatography
 HFIP—hexafluoroisopropanol
 IR—infrared spectrum
 NMR—nuclear magnetic resonance spectrum
 PET—poly(ethylene terephthalate)
 PS—polystyrene
 THF—tetrahydrofuran
 TMS—tetramethylsilane

EXAMPLE 1

2,2-Bis(Trifluoromethyl)-1,3-Dioxolan-4-oyl Chloride

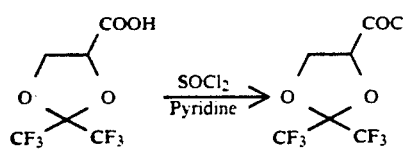

2,2-Bis(trifluoromethyl)-1,3-dioxolan-4-oyl chloride was prepared from 2,2-bis(trifluoromethyl)-4-carboxy-1,3-dioxolane (see U.S. patent application 07/401,668, filed Aug. 30, 1989) (25.4 g, 0.1 mole). To this substrate was added pyridine (3.16 g, 0.04 mole) followed by thionyl chloride (14.3 g, 0.12 mole), with external cooling to maintain the pot at ambient temperature. When the addition was complete, the reaction mixture was heated slowly to 70° C. for 1.5 hour, then at 90° to 100° C. for 0.5 hour. The product was distilled from the reaction mixture, a clear colorless liquid, 22.0 g (81% yield) was obtained. Bp. 50° C./10 mm. $^1$H-NMR (Neat): $\delta$ 5.23 (t, J=7.0 Hz, 1H), 4.73 (m, 2H); $^{19}$F NMR (neat): −80.5 (q, J=8.5 Hz, 3F), −81.5 (q, J=8.5 Hz, 3F). Anal. Calc. for $C_6H_3ClF_6O_3$: C: 26.44, H: 1.11, F: 41.83, Cl: 13.00; Found: C: 26.13, H: 1.11, F: 41.44, Cl: 13.38.

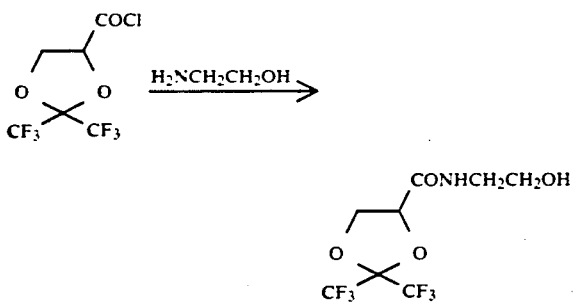

2,2-Bistrifluoromethyl-1,3-dioxolane-4-oyl chloride (50.57 g, 0.186 mole) was added dropwise to the mixture of ethanolamine (11.34 g, 0.186 mol), triethylamine (18.56 g, 0.183 mole) and anhydrous dichloromethane (200 ml) maintained at −5° to 5° C., with stirring, under nitrogen. The reaction was stirred overnight. The product mixture was washed with 150 ml of saturated NaCl solution 3 times, then dried over anhydrous sodium sulfate. A brown colored paste 51.45 g was obtained after evaporating the dichloromethane solvent. The mixture was then purified by distillation under vacuum to give 19.4 g of colorless liquid. The boiling point was 111.2°-111.5° C./0.1 mm. The structure of the compound was characterized by $^1$H-NMR as well as IR.

$^1$H-NMR ($\delta$ ppm, CDCl$_3$, TMS):
2.72 (s, br, 1H, —OH),
3.50 (m, 2H, NH—CH2—CH2—OH),
3.75 (m, 2H, NH—CH2—CH2—OH),
4.34 (t, J=7.9 Hz, 1H, —OCHaHb—CH—O,
4.70 (t, J=7.9 Hz, 1H, —OCHaHb—CH—O),
4.95 (t, J=7.7 Hz, 1H, O—CH—CH2—O),
6.89 (s, br, 1H, —NH),
IR (neat): 3400 cm$^{-1}$ (OH), 1680 cm$^{-1}$(C(O)NH).

Thionyl chloride (15.21 g, 0.128 mole) was added dropwise to the previously prepared compound (19.0 g, 0.064 mole) in dichloromethane (50 ml), at −5° C. to 5° C., with stirring, under nitrogen. The reaction was carried out for 2 hours at 5° C., then heated up to room temperature gradually. After removal of dichloromethane by evaporation, the chlorinated compound was isolated by the distillation (Bp. 83.2° C./0.8 mm). The yield was 65.9%.

$^1$H-NMR ($\delta$ ppm, in CDCl$_3$ with TMS):
3.64 (m, 4H, —NH—CH2CH2—Cl),
4.34 (t, 8.1 Hz, 1H, —OCHaHb—CH—O),
4.71 (t, 8.0 Hz, 1H, —OCHaHb—CH—O),
4.95 (t, 7.7 Hz, 1H, —OCH2—CH—O),
6.80 (s, br, 1H, NH).
IR (neat): 1690 cm$^{-1}$ (C(O)NH).

MeOH (20 ml) was added to the chlorinated compound (9.28 g, 29.44 mmole), then sodium hydroxide pellets (1.73 g, 43.3 mmole) were added into the mixture. The mixture was stirred at room temperature for 2 hours. After removing the MeOH, dichloromethane (30 ml) and saturated NaCl solution (20 ml) were added to the reaction mixture. Extraction was carried out and the organic layer was collected. The same procedure was repeated twice by adding 30 ml of dichloromethane for each extraction. The organic portions obtained were combined and dried over sodium sulfate. After evaporating the solvent, 7.52 g of the desired oxazoline, a yellow colored liquid, was obtained. The compound was then purified by distillation under vacuum (Bp. 61° C./0.25 mm). The yield was 7.45 g (71.0%).

$^1$H-NMR ($\delta$ ppm, in CDCl$_3$ with TMS):
3.94 (t, J=9.7 Hz, N—CH2, 2H),
4.40 (t, J=9.2 Hz, O—CH2, 2H),
4.50 (t, J=7.9 Hz, O—CHaHb—CH—O, 1H),
4.57 (t, J=7.3 Hz, O—CHaHb—CH—O, 1H),
5.07 (t, J=7.2 Hz, O—CH2—CH—O, 1H).
$^{19}$F-NMR: −−80.5, 81.0 ppm
IR (neat): 1680 cm$^{-1}$ (O—C=N—), 1240 cm$^{-1}$ (C-F).

Elemental Analysis (Calculated as $C_8H_7F_6NO_3$):
Found: C 34.30%, H 2.52%, F 40.36%, N 4.99%.
Calcd: C 34.42%, H 2.53%, F 40.84%, N 5.02%.

EXAMPLE 2

Synthesis of
2-(Perfluoro-2,4-Dioxolanyl)-ethyl-2-Oxazoline

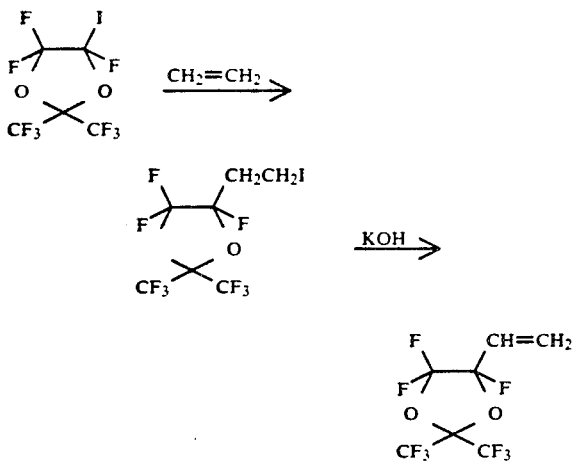

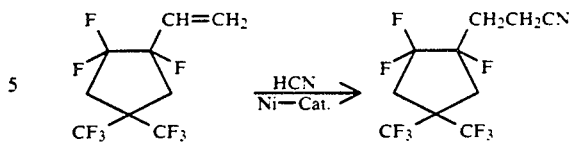

In a shaker tube was charged perfluoro-2,2-dimethyl-1,3-dioxole (see U.S. Pat. Nos. 3,865,845 and 3,978,030) (48.8 g, 0.2 mole), mercury (II) oxide (yellow-form, 45 g, 0.208 mole), iodine (127 g, 0.5 mole), phenothiazine (0.1 g), and hydroquinone (0.055 g). The tube was cool-evacuated and hydrogen fluoride (12 g, 0.6 mole) was transferred into the tube. The tube was sealed and was heated at 50° C./2 hours, then the temperature was raised from 50° C. to 125° C. in 2 hours and was kept at 125° C. for another 3 hours. The product mixture was carefully dumped into ice water, the bottom organic layer was separated. The 2,2-bis(trifluoromethyl)-4-iodo-4,5,5-trifluoro-1,3-dioxolane was purified by distillation. The desired product was obtained as a clear, colorless liquid, yield 50 g (64%). Bp. 74°–76° C. 19F NMR (Neat): −46.6 (m, br, 1F), −60.4 (dm, J=129 Hz, 1F), −87.1 (dm, J=129 Hz, 1F), −80.9 (s, br, 6F).

2,2-Bis(trifluoromethyl)-4-iodo-4,5,5-trifluoro1,3-dioxolane (11.7 g, 0.03 mole) was mixed with ethylene (5 g, 0.179 mole) in a 75 ml shaker tube. The tube was sealed and heated at 220° C. for 10 hours. The product mixture was distilled to afford 2,2-bis(trifluoromethyl)-4-iodoethyl-4,5,5-trifluoro-1,3-dioxolane as a light pink liquid with a boiling point of 95° C./100 mm. $^1$H-NMR (neat) δ 2.90 (m, 2H), 3.43 (m, 2H); $^{19}$F NMR (Neat): −110.0 (m, 1F), −77.8 (dm, J=137.5 Hz, 1F), −88.3 (dd, J=137.5 Hz, 8.5 Hz, 1F), −80.9 (m, 3F), −81.6 (m, 3F).

2,2-Bis(trifluoromethyl)-4-(2-iodoethyl)-4,5,5-trifluoro-1,3-dioxolane (16.72 g, 0.04 mole) was mixed with 10M KOH (20 ml, 0.20 mole) and bis(2-hydroxypropyl) benzyl dodecyl ammonium chloride phase transfer catalyst (60% w/w aqueous solution, 0.855 g, 0.002 mole) and was vigorously stirred at room temperature. The reaction was monitored by gas chromatography and was stopped when the conversion of the starting material was complete. The bottom organic layer was separated, washed with water and diluted HCl, then distilled to afford 2,2- bis(rifluoromethyl)-4-vinyl-4,5,5-trifluoro-1,3dioxolane 9.5 g (82% yield) as a clear, colorless liquid. Bp. 70°–72° C. $^1$H-NMR (neat): δ 5.40–5.90 (m); $^{19}$F NMR (neat): −112.8 (m, 1F), −75.7 (dm, J=140 Hz, 1F), −90.3 (dd, J=140, 10.5 Hz, 1F), −82.0 (m, 3F), −82.6 (m, 3F).

A mixture comprised of Ni[P(O-tolyl)3]4 (3.3 g, 2.2 mmole) and P(O-tolyl)3 (1.7 g, 4.8 mmole), 2,2-bis(trifluoromethyl)-4-vinyl-4,5,5-trifluoro-1,3-dioxolane (30 g, 0.103 mole), 25% EtAlCl2 in toluene (2.0 ml), and toluene (25 ml) was heated under nitrogen in an oil bath at 60° C. A 50% HCN in toluene solution was fed from an ISCO pump at a rate of 1.5 ml/hour for 4.5 hours and then 0.5 ml/hour overnight until the reaction was complete (GC determination). The mixture was allowed to cool and was purified by distillation to give 2,2- bis(trifluoromethyl)-4-(2-cyanoethyl)-4,5,5-trifluoro1,3-dioxolane as a clear, colorless liquid in 66% yield. Bp. 65°–68° C./7.0 mm. $^1$H-NMR (CDCl$_3$): δ 2.72 (t, J=7.8 Hz, 2H), 2.50 (m, 2H); $^{19}$F NMR (CDCl$_3$): −110.2 (m, 1F), −76.9, −77.6 (2m, 1F), −87.0, −87.7 (2d, J=9.3 Hz, 1F), −80.6 (m, 3F), −81.3 (m, 3F). Anal. Calc. for C$_8$H$_4$F$_9$NO$_2$: C: 30.28, H: 1.27, F: 53.94; Found: 30.21, H: 1.34, F: 54.26. MS: [M] Calc.: 317.0098; Found: 317.0081; MS (PCI): [M+H]: Calc.: 318.0177; Found: 318.0176.

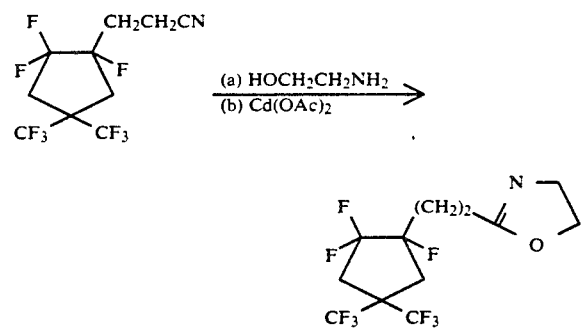

2,2-Bis(trifluoromethyl)-4-(2-cyanoethyl)-1,3dioxolane (10 g, 31.55 mmole), ethanolamine (1.93 g) and Cd(OAc)$_2$.2H$_2$O (0.421 g, 1.58 mmole) were added to a predried 25 ml flask with stirring The reaction mixture was then heated up at 130° C. for 20 hours. All the compounds that distilled under vacuum (20 mmHg) at 100° C. were collected in the same flask. The liquid obtained was then purified by redistillation. 2-(Perfluoro-2,4-dioxolanyl)ethyl-2-oxazoline was obtained at 94.7°–95.7° C. (25 mmHg). The yield was 7.36 g (64.6%).

$^1$H-NMR (δ ppm, CDCl$_3$, TMS):
2.41–2.60 (m, 4H, —CH2CH2—),
3.85 (t, J=9.5 Hz, 2H, —NCH2—CH2O—),
4.28 (t, J=9.5 Hz, 2H, —NCH2—CH2O—),
IR (neat): 1700 cm$^{-1}$(—N=C—O), absence of 2350 cm$^{-1}$ (—CN).

Elemental Analysis (Calculated as C$_{10}$H$_8$F$_9$NO$_3$):
Found: C 33.22%, H 2.12%, F 47.42%, N 3.89.
Calcd: C 33.26%, H 2.23%, F 47.34%, N 3.88%.

EXAMPLES 3–7

The final product of Example 1 was polymerized under various conditions. A typical polymerization run is illustrated below:

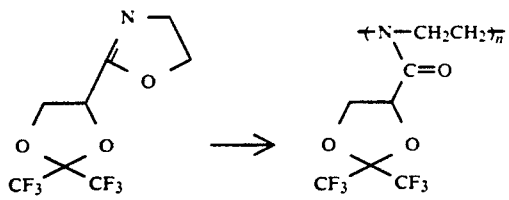

The Oxazoline (0.63 g, 2.26 mmole) was charged to a 25 ml pre-dried ampul under nitrogen. Then methyl p-toluenesulfonate (MeOTs) (0.0167 g) was introduced by micro-syringe with vigorous stirring The ampul was then sealed and kept to 90° C. oil bath for 24 hrs. During polymerization, the reaction mixture solidified. Chloroform (20 ml) was added to dissolve the solid then a small amount of n-butylamine (1-2 ml) was added to quench the polymer reaction The solution was then poured into hexane (100 ml) to precipitate the polymeric material, but due to the high solubility of the polymer, a large amount of polymer was also recovered from supernatant. In this case, 0.14 g of polymer was obtained from precipitation and 0.47 g of polymer was recovered from supernatant. Total polymer yield is 94.3%.

Polymer structure was characterized by $^1$H-NMR, IR and GPC (HFIP eluent with PET standard).

$^1$H-NMR (δ ppm, CDCl$_3$ with TMS): 3.53 (s, br, —NCH2CH2—), 4.30 (s, br, —O—CHaHb—CH—O—), 4.65 (s, br, —O—CHaHb—CH—O—), 4.81 (s, br, —O—CH—CH2—O—), IR(neat): 1670 cm$^{-1}$(C(O)N—)

The results of the various polymerizations are summarized in Table I.

TABLE I

| Example[a] | Oxazolone (m mol) | MeOTs (m mol) | Solvent | Yield[c] (%) | Mw[e] | MWD[e] |
|---|---|---|---|---|---|---|
| 3 | 2.26 | 0.090 | — | 94.3 | 17700 | 3.13 |
| 4 | 1.98 | 0.087 | DMF | 89.1 | 8830 | 5.04 |
| 5 | 1.69 | 0.068[b] | — | 100 | 14500 | 7.41 |
| 6 | 2.03 | 0.012 | — | 91.5 | 7220 | 3.29 |
| 7 | 2.12 | 0.086 | CHCl$_3$ | 41.2[d] | 6190 | 4.21 |

[a]Polymerized at 90° C. for 48 hours
[b]BF$_3$.OEt$_2$ was used as initiator
[c]Total yields of precipitate and dry residue of supunatant from hexane solution
[d]The yield of precipitate
[e]Measured by GPC in HFIP with PET as standard

EXAMPLES 8-11

Polymerization of 2-(Perfluoro-2,4-Dioxolanyl)ethyl-2-Oxazoline

Polymerizations were carried out under various conditions. A typical polymerization run is illustrated below:

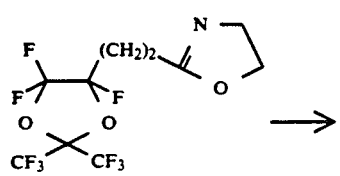

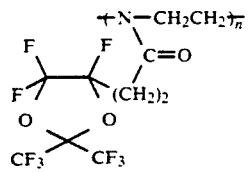

The oxazoline monomer (0.58 g, 1.6 mmole) was charged to a pre-dried 20 ml ampoule by syringe. Then methyl p-toluenesulfonate (MeOTs) (0.015 g, 0.08 mmole) was added dropwise to the monomer, with stirring under nitrogen. The mixture was cooled in ice-water and the ampoule was sealed. After heated the ampoule at 90° C. for 24 hours (the solution solidified within 2 hours), hexafluoroisopropanol (HFIP) (10 ml) was added to dissolve the reaction mixture. Then n-butylamine (1 ml) was added to quench the polymer reaction. The product mixture was then poured slowly into hexane (100 ml) to precipitate the polymeric material. White powdered polymer 0.52 g (87.7%) was isolated after filtration. Polymer 0.06 g (10.1%) was recovered from the supernatant.

The polymer structure was characterized by $^1$H-NMR, IR, elemental analysis, and GPC (THF eluent with PS standard).

$^1$H-NMR (δ ppm, in CDCl$_3$ with TMS):
2.3-2.7 (br, 2H, —C(O)CH2CH2—),
3.5 (br, 2H, —NCH2CH2—), and small peaks from MeOTs and n-butylamine moieties.
MeOTs: δ 3.06 (s, CH3—Ph—), 7.01 and 7.75 (d, Me—C6H4—SO3—),
BuNH$_2$: δ 0.93 (t, CH3—), 1.26 (q, Me—CH2—), 1.46 (m, Et—CH2—),
IR (neat): 1650 cm$^{-1}$(C(O)N—)
Elemental Analysis (Calculated as C$_{10}$H$_8$F$_9$NO$_3$).
Found: C 33.12%, H 2.29%, N 3.73%, F 47.25%.
Calcd: C 33.26%, H 2.23%, N 3.88%, F 47.34%.

The results of the various polymerizations are summarized in Table II.

TABLE II

| Example[a] | Oxazolone (m mol) | MeOTs (m mol) | Solvent | Yield[b] (%) | Mw[c] | MWD[c] |
|---|---|---|---|---|---|---|
| 8 | 1.60 | 0.080 | — | 87.7 | 5190 | 1.16 |
| 9 | 1.49 | 0.064 | CHCl$_3$ | 43.2 | 4650 | 1.10 |
| 10 | 1.62 | 0.004 | — | 95.6 | 5730 | 1.13 |
| 11 | 2.01 | 0.005 | CHCl$_3$ | 75.6 | 4490 | 1.05 |

[a]Polymerized at 90° C. for 24 hours
[b]Precipitated in hexane
[c]Measured by GPC in THF with PS as standard

EXAMPLE 12

Preparation of 2,2-Bis(Trifluoromethyl)-4-Vinyl-1,3-Dioxolane

Butadiene monoepoxide (9.8 g, 0.14 mole, Aldrich Chemical Co.) was mixed with hexafluoroacetone (50 g, 0.30 mole) in a 210 ml Hastelloy ®C shaker tube in the presence of tetrabutylammonium bromide (0.12 g) and water (0.12 g). The tube was sealed and heated at 80° C. for 1 hour, 100° C. for 1 hour and 120° C. for 6 hours. The product mixture was distilled to afford the desired 2,2-bis(trifluoromethyl)-4-vinyl-1,3-dioxolane, 4.0 g (12.1% yield), as a clear, colorless liquid. Bp. 78°–80° C. $^1$H-NMR (CDCl$_3$): δ 5.84 (m, 1H), 5.48 (m, 2H), 4.88 (dd, J=6.6, 5.4 Hz, 1H), 4.46 (t, J=6.6 Hz, 1H), 3.87 (t, J=6.6 Hz, 1H).

EXAMPLE 13

A nylon 6,6 in HFIP solution is made by dissolving 0.5 g of nylon pellet in 9.5 g of HFIP. A nylon film was cast from this solution on a glass plate. After the evaporation of solvent, the water contact angle of the nylon film was measured 57 deg. A 10 wt. % of fluorinated oxazoline polymer (from Example 9) in chloroform solution was then added dropwise to just cover the dry film surface. The water contact angle was then measured after all the solvent was evaporated. The water contact angle on the polyoxazoline coated nylon film surface increased to 95 deg.

Although preferred embodiments of the invention have been described hereinabove, it is to be understood that there is no intention to limit the invention to the precise constructions herein disclosed, and it is to be further understood that the right is reserved to all changes coming within the scope of the invention as defined by the appended claims.

What is claimed is:

1. A compound of the formula

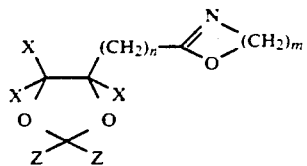

wherein:

each X is independently hydrogen, chlorine or fluorine;

each Z is independently $-CY_3$, $-C_2Y_5$, normal $-C_3Y_7$, fluorine, or chlorine;

m is 2 or 3;

n is zero or an integer of 1 to 10;

each Y is independently chlorine or fluorine; and provided that at least one of Y is fluorine.

2. The compound as recited in claim 1 wherein said m is 2.

3. The compound as recited in claim 2 wherein each said X is independently fluorine or hydrogen.

4. The compound as recited in claim 2 wherein both said Z are $-CY_3$.

5. The compound as recited in claim 2 wherein each said Y is fluorine.

6. The compound as recited in claim 3 wherein each said Y is fluorine.

7. The compound as recited in claim 4 wherein each said Y is fluorine.

8. The compound as recited in claim 3 wherein said n is 0, 2, or 4.

9. The compound as recited in claim 2 wherein all said X groups are fluorine.

10. The compound as recited in claim 2 wherein all said X groups are hydrogen.

11. The compound as recited in claim 5 wherein all said X groups are fluorine.

12. The compound as recited in claim 5 wherein all said X groups are hydrogen.

13. The compound as recited in claim 2 which is 2-{2-[perfluoro(2,2-dimethyl-4-dioxolanyl)]ethyl}oxazoline or 2-[2,2-bis(trifluoromethyl)-4-dioxolanyl]-oxazoline.

* * * * *